United States Patent
Fischer et al.

(10) Patent No.: US 6,908,491 B2
(45) Date of Patent: Jun. 21, 2005

(54) SYSTEM AND METHOD FOR COLOR-REVITALIZING HAIR

(75) Inventors: Vince Fischer, Cincinnati, OH (US); Masahiko Sakai, Tokyo (JP); Satoshi Onitsuka, Tokyo (JP); Hajime Miyabe, Tokyo (JP); Hiroshi Ikeda, Tokyo (JP); David Ferguson, Covington, KY (US)

(73) Assignee: The Andrew Jergens Company, Cincinatti, OH (US)

( * ) Notice: Subject to any disclaimer, the term of this patent is extended or adjusted under 35 U.S.C. 154(b) by 241 days.

(21) Appl. No.: 09/983,070

(22) Filed: Oct. 23, 2001

(65) Prior Publication Data

US 2003/0074746 A1 Apr. 24, 2003

(51) Int. Cl.$^7$ ................................................. A61K 7/13
(52) U.S. Cl. ........................ 8/405; 8/406; 8/441; 8/454; 8/455; 8/459; 8/462; 8/463
(58) Field of Search ............................. 8/405, 406, 441, 8/459, 454, 455, 462, 463

(56) References Cited

U.S. PATENT DOCUMENTS 5,643,341 A * 7/1997 Hirsch et al. .................. 8/405
5,690,921 A * 11/1997 Lang et al. .............. 424/70.13
5,843,193 A    12/1998 Hawkins et al. ................ 8/408

FOREIGN PATENT DOCUMENTS

EP    0 970 685 A1  * 12/2000  ............ A61K/7/13
JP      60152408 A  *  8/1995  ............ A61K/7/13

OTHER PUBLICATIONS

ColorStay® Permanent Cream–Gel Haircolor, ©1999 Revlon Consumer Products Corporation, 1 page.
Silver Edge Beauty Supply, MultiBEAUTY.com, A Division of Silver Edge Co., http://mall.weborder.com, pp. 1–6.
ColorPlus, Tricostyle.com, www.tricostyle.com/HTML/colorPlus.html, 4 pages.

* cited by examiner

*Primary Examiner*—Lorna M. Douyon
*Assistant Examiner*—Eisa Elhilo
(74) *Attorney, Agent, or Firm*—Piper Rudnick LLP; Steven B. Kelber

(57) ABSTRACT

A method for color-revitalizing a color tone of hair that involves applying a color-revitalizing composition to hair previously dyed with an oxidative hair dye composition. The color-revitalizing composition, which has a color determined by the color of the oxidative hair dye composition and contains at least one direct dye, revitalizes the color tone originally obtained by after dyeing with the oxidative hair dye composition.

24 Claims, 14 Drawing Sheets

(14 of 14 Drawing Sheet(s) Filed in Color)

SYSTEM AND METHOD FOR COLOR-REVITALIZING HAIR

BACKGROUND OF THE INVENTION

1. Field of the Invention

The present invention relates to a color-revitalizing system and method for returning the faded color tone of hair previously dyed with an oxidative hair dye composition to the color tone observed immediately after dyeing. The system and method of the invention are able to cope with widely diverse color tones.

2. Description of the Background Art

It is well appreciated that individuals often wish to cosmetically alter the coloring of their hair by various known hair coloring treatments and that many individuals change their own hair color to their favorite hair color using currently available hair dye compositions. In particular, oxidative dye compositions are commonly used because such compositions simultaneously decolor and dye hair, thus widening the degree of freedom of hair color. Thus, individuals having comparatively dark hair are able to use such products. Moreover, the products provide a greater number of color variations.

Use of oxidative dye compositions to treat hair is typically not inexpensive and is time consuming as well. Moreover, the chemicals employed in these treatments can be caustic and somewhat damaging to the hair. Their frequent use is not preferred, and rather they are generally used at intervals of at least about one month. It is unavoidable that the color of hair dyed with oxidative dye compositions gradually fades during this one month owing to the influence of washing with shampoo, sweat, ultraviolet rays from sunshine and the like. The gradual fading of color results in a gradual reduction in the feeling of satisfaction generally felt immediately after dyeing.

Thus, individuals who have had their hair color-treated are often desirous of prolonging the effects of treatment for as long as possible, and otherwise wish to keep their hair in as healthy a state as possible between visits to the colorist. One way of prolonging the freshness of a hair coloring treatment and to otherwise preserve the condition of the hair is to use hair color maintenance shampoos, conditioners, rinses, mousses, gels, sprays and the like. Examples of such hair color maintenance products include AVEDA™ shampoos and conditioners; TRICOL™ Color Plus™ products; LOGICS™ Color Refresher™; and UTENA™ Cha Charl™. Such hair color maintenance products are typically formulated with a degree of coloring, so as to assist an individual in an attempt to prolong the duration of the coloring treatment.

Thus, products for maintaining hair color without damaging hair are already being sold, and products such as shampoos, conditioners or sets thereof, which have been designed to be used every day for hair previously dyed with an oxidative dye composition, are known. However, products having the same color as the color of the hair dyed with permanent (oxidative) hair dye to maintain color of the dyed hair is often selected. The products, typically referred to as color-maintaining products, are formulated having the same color as the dyed hair. Such products have a number of drawbacks. For example, such products require daily use in order to maintain hair color. Furthermore, such products are low in hair dyeing power, thus being insufficient for revitalizing fading color.

U.S. Pat. No. 5,643,341 discloses a method for more exactly maintaining hair at the color observed immediately after being dyed with an oxidative hair color composition. More specifically, the method involves determining hair color and tone by visual recognition, applying the observed color and tone to a chart to select at least two products to be used; mixing the selected products; and applying the selected products to the individual's hair, thereby maintaining the color of hair observed immediately after being dyed with an oxidative dye composition. Color refreshing rinse sold by Revlon Co. under the name of ROUX® Fancifull® is a known temporary hair dye product whose color is provided according to visual recognition of hair color.

However, this method is not always sufficient in returning hair to the exact color observed immediately after being dyed with an oxidative dye composition because the color of compositions that should be used to return faded hair color to the color of hair observed immediately after dyeing may be different for different individuals even in cases where the color of hair determined by visual recognition appears to be the same. For example, even in persons whose hair colors are almost the same "somewhat reddish light brown" as determined by visual recognition, colors of compositions that should be used for exactly returning hair to the color observed immediately after dyeing when the hair color of the "somewhat reddish light brown" is faded are different between a person who has dyed her original blond hair "somewhat reddish light brown" and a person who has dyed her original somewhat dark reddish brown hair "somewhat reddish light brown".

As described above, conventional color maintaining products are designed to supply the same color to return one's hair to the color of dyed hair. Such products have required selection of color by visual recognition. With respect to the finish, it is difficult to return the hair color to the color of dyed hair.

There thus remains a need to supply color lost by washing or shampooing.

Hair dyeing is based on a reaction between precursors and couples resulting in the production of many coloring compounds that differ in washing out properties. The present inventors have observed that fading of dyed hair is caused mainly by shampooing, which results in washing out of certain color components of hair dye. Some coloring components are more easily washed out during shampooing. This washing out causes both fading and change of tone of dyed hair. The present inventors have discovered a system and method that are capable of supplying washed out color components to dyed hair. The system and method of the invention involve the selection of color-maintaining products based on dyeing characteristics of hair dyes rather than on the color of dyed hair. The system and method of the invention are different from prior methods in that the inventive system is not dependent on providing the same color as the dyed hair.

SUMMARY OF THE INVENTION

It is an object of the present invention to provide a system and method that can conveniently be used as a color revitalizer to compensate for the gradual color fading observed after permanent color treatments.

It is another object of the present invention to return hair that has previously been dyed with an oxidative dye composition and that has faded to the color originally observed immediately after being dyed.

It is yet another object of the present invention to provide a system and method that are able to cope with varied color tones in spite of their diversity and are able to exactly achieve the original color tone observed immediately after dyeing.

It is a further object of the present invention to avoid frequent hair dyeing for the purpose of revitalizing hair color to prevent hair from being damaged. It is yet a further object of the present invention to improve dullness and to impart a feeling of transparency, luster, brightness, voluminousness, deep shade and moisture to previously color treated hair.

Yet another object of the present invention is to provide a system and method which are safe and do not irritate or stain the skin.

The present inventors have discovered a color-revitalizing system and method, in which a color-revitalizing composition is selected based on the color of an oxidative dye composition previously used to dye the subject hair, wherein the original color obtained using the oxidative dye composition is revitalized and able to be maintained until the next scheduled hair dyeing, even if the subject hair had achieved a color-faded stage.

According to the present invention, there is thus provided a system and method for color-revitalizing a color tone of hair that involves applying a color-revitalizing composition that has a color determined by the color of an oxidative hair dye composition previously used in hair dyeing and that contains at least one direct dye to hair that has previously been treated by the oxidative hair dye composition.

The system and method of the invention permit a user to revitalize fading hair at anytime as often as the user deems necessary without damaging hair. In addition, the system and method of the invention remove the requirement of visual recognition of color variation. By providing a limited number of color classifications, the system and method of the invention remove the burdensome "mix and match" requirement employed in prior methods.

BRIEF DESCRIPTION OF THE DRAWINGS

The file of this patent contains at least one drawing executed in color. Copies of this patent with color drawings will be provided by the Patent and Trademark Office upon request and payment of the necessary fee.

DETAILED DESCRIPTION OF THE INVENTION

Figure 1:
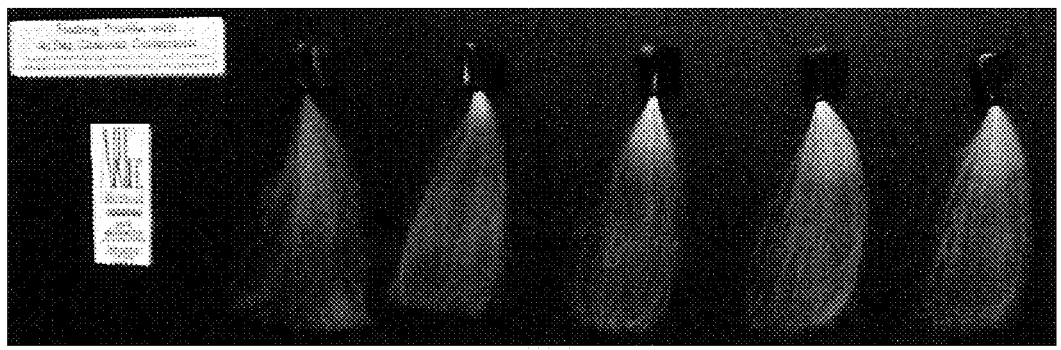
FIG. 1 is a photograph of hair locks showing fading overtime of hair color treatment using ArTec™.
Figure 2:
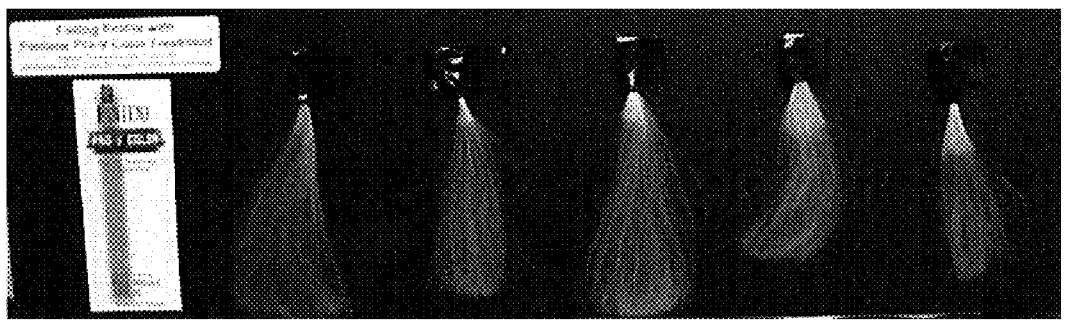
FIG. 2 is a photograph of hair locks showing Cading over time of hair color treatment using Pantene Pro-V™.
Figure 3:
FIG. 3 is a photograph of hair locks showing fading over time of hair color treatment using Color VIVE™.
Figure 4:
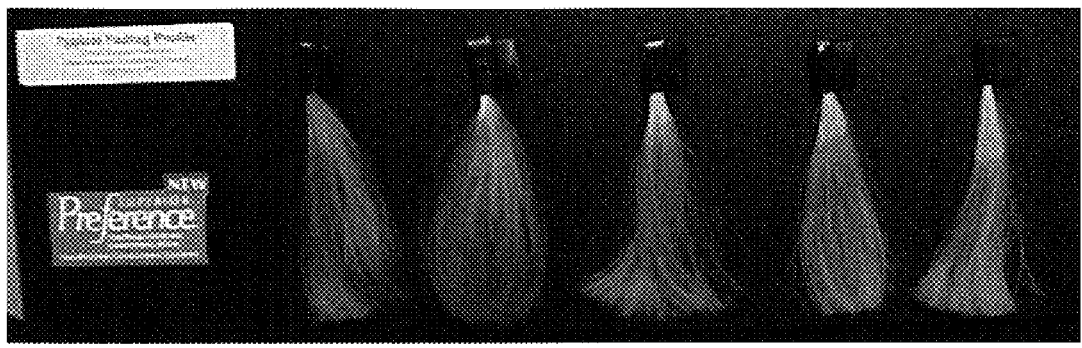
FIG. 4 is a photograph of hair locks showing fading over time of hair color treatment using Preference™.
Figure 5:
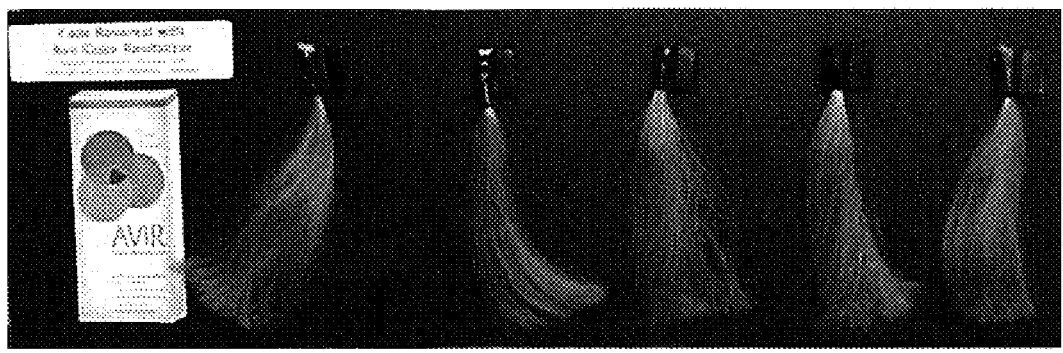
FIG. 5 is a photograph of hair locks showing fade reversal over time of color-treated hair after treatment in accordance with the invention.
Figure 6:
FIG. 6 is a photograph of hair locks that were originally treated with L'Oreal Rouge Roinantiques™ and over time demonstrated fading. Following treatment of the faded hair with a red color in accordance with the invention, the hair regained the color observed immediately after the original treatment with L'Oreal Rouge Romantiques™.
Figure 7:
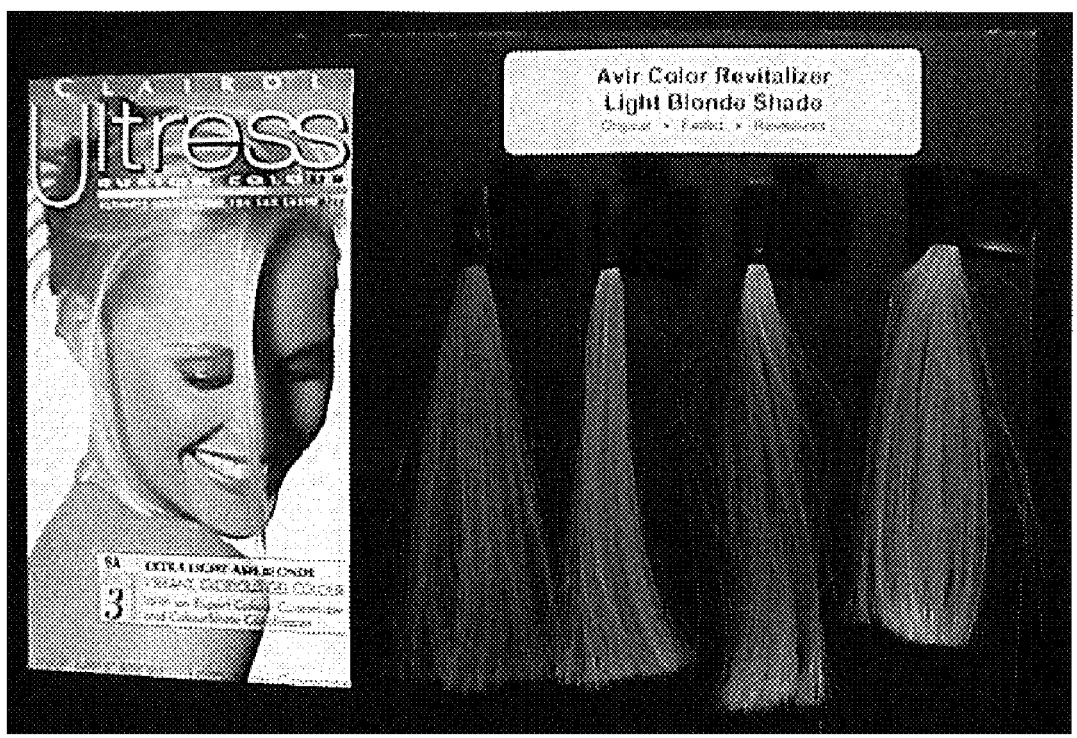
FIG. 7 is a photograph of hair locks that were originally treated with Ultras Custom Colour™ and over tune demonstrated fading. Following treatment of the faded hair with a light blonde color in accordance with the invention, the hair regained the color observed immediately after the original treatment with Ultress Custom Colour™.
Figure 8:
FIG. 8 is a photograph of hair locks that we originally treated with L'Oreal Superior Preference™ and over time demonstrated fading. Following treatment of the faded hair with a light auburn color in accordance with the invention, the hair regained the color observed immediately after the original treatment with L'Oreal Superior Preference™.
Figure 9:
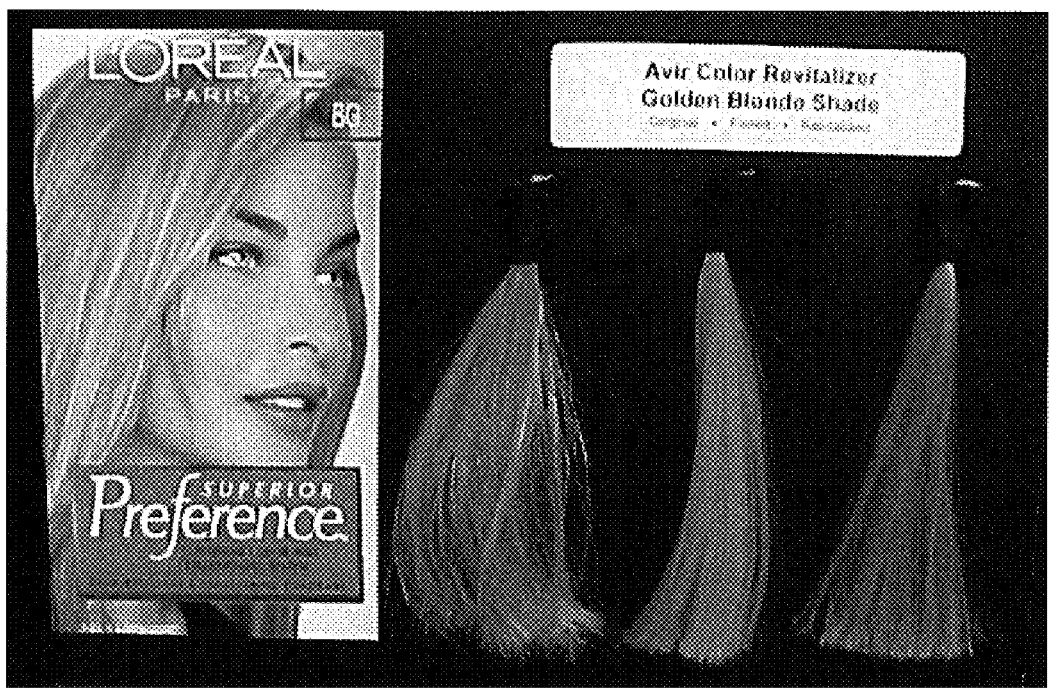
FIG. 9 is a photograph of hair locks that were originally treated with L'Oreal Superior Preference™ and over time demonstrated fading. Following treatment of the faded hair with a golden blonde color in accordance with the invention, the hair regained the color observed immediately after the original treatment with L'Oreal Superior Preference™.
Figure 10:
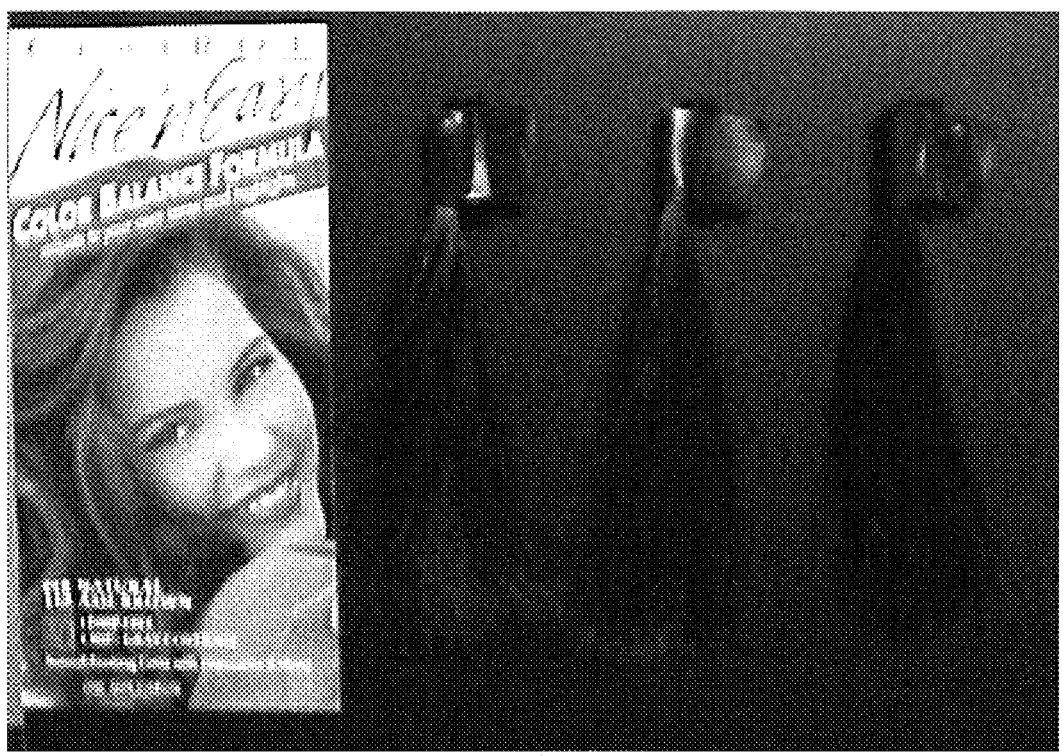
FIG. 10 is a photograph of hair locks that were originally treated with Nice'n Easy Color Balance Formula™ and over time demonstrated fading. Following treatment of the faded hair with an ash brown color in accordance with the invention, the hair regained the color observed immediately after the original treatment with Nice'n Easy Color Balance Fonnula™.
Figure 11:
FIG. 11 a photograph of hair locks that were originally treated with L'Oreal Furia™ and over time demonstrated fading. Following treatment of the faded hair with a auburn color in accordance with the Invention, the hair regained the color observed immediately after the original treatment with L'Oreal Feria™.
Figure 12:
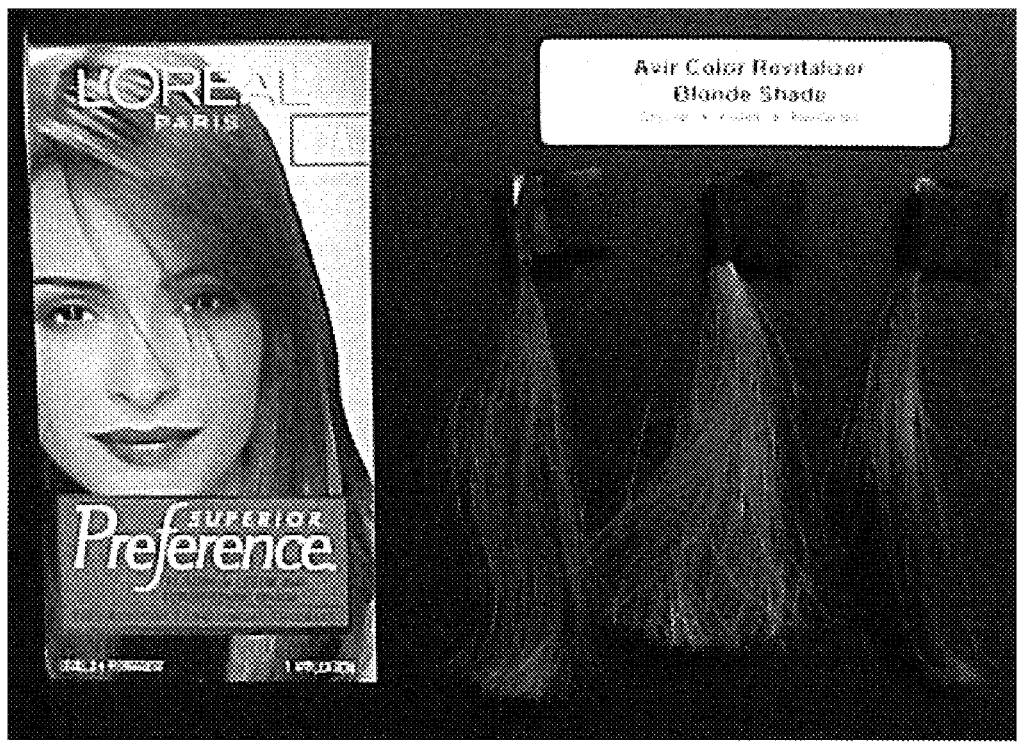
FIG. 12 is a photograph of lair locks that were originally treated with L'Oreal Superior Preference™ and over time demonstrated fading. Following treatment of the faded hair with a blonde color in accordance with the invention, the hair regained the color observed immediately after the original treatment with L'Oreal Superior Preference™.
Figure 13:
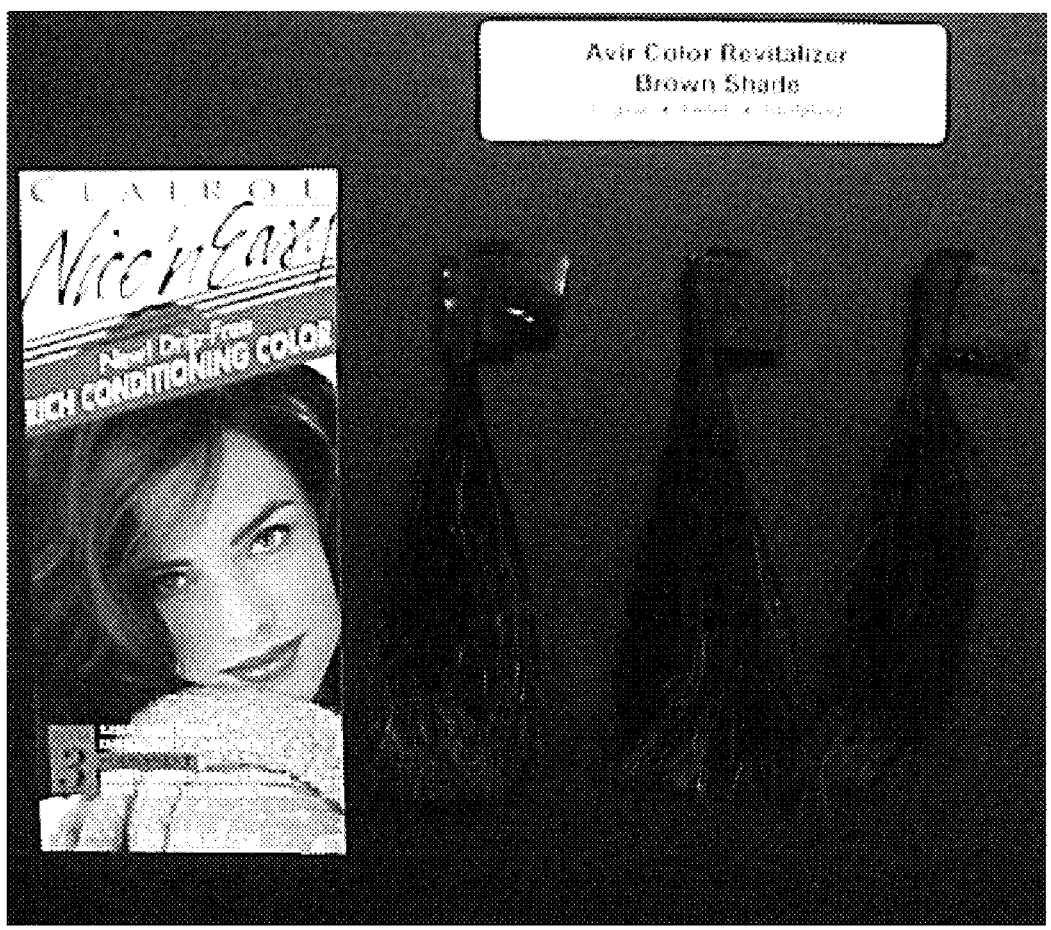
FIG. 13 is a photograph of hair locks that were originally treated with Nice'n Easy Rich Conditioning Color™ and over time demonstrated fading. Following treatment of the faded hair with a brown color in accordance with the invention, the hair regained the color observed immediately after the original treatment with Nice'n Easy Rich Conditioning Color™.
Figure 14:
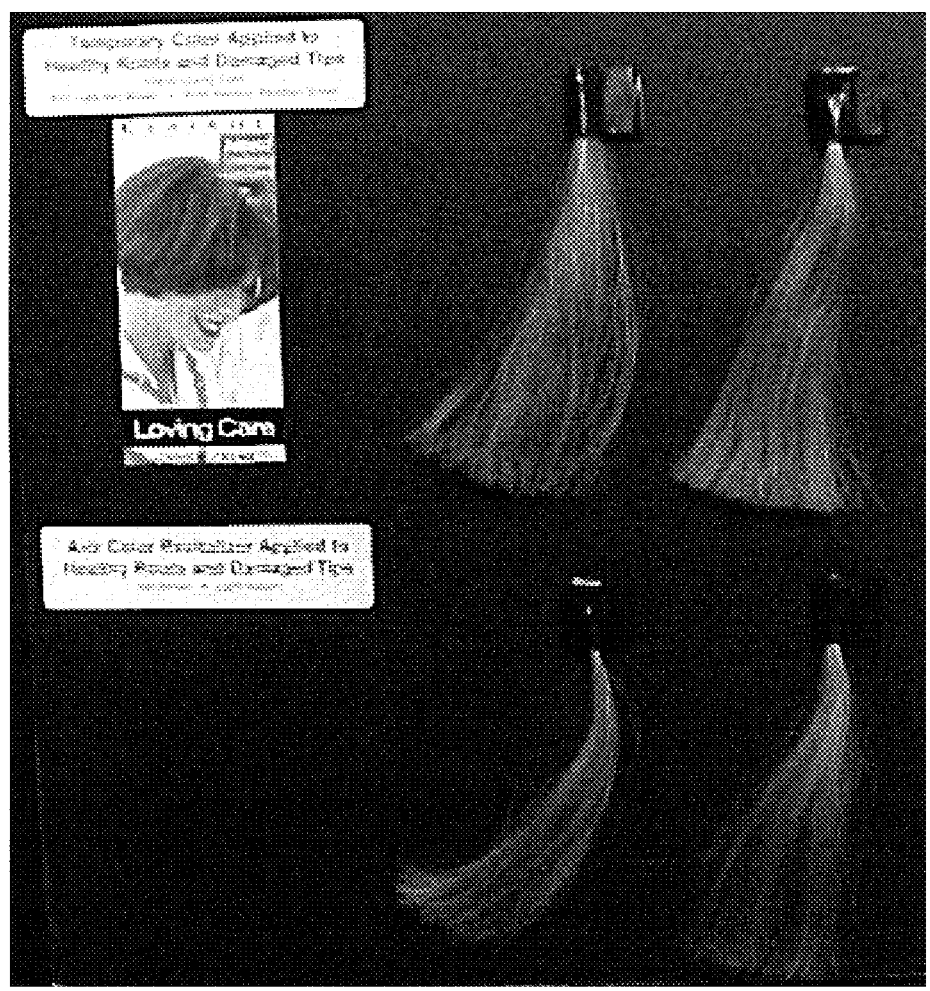
FIG. 14 is a photograph of hair locks comparing hair after treatment using Loving care™ (A) and after treatment in accordance with the invention (B).

According to the invention, the color of a color-revitalizing composition that can be used to color-revitalize the faded color tone of hair previously dyed with an oxidative hair dye composition to the original color tone observed immediately after dyeing is selected based on the color of the oxidative dye composition originally used to dye the hair.

The color-revitalizing composition of the invention enriches hair color by replacing faded color elements and by eliminating dull tones. The color-revitalizing composition of the invention is non-damaging and returns hair to the original color tone dyed with the oxidative dye.

The present inventors have discovered a corresponding relationship between the color of the oxidative hair dye composition and the color of the color-revitalizing composition. Even if a color of a composition used to return hair to the color tone observed immediately after dyeing with the oxidative hair dye composition cannot be exactly selected by the above-described "selection method based on the visual recognition of hair color," the color of the composition can be exactly selected according to the system and method of the present invention and can exactly revitalize hair to the color tone observed immediately after dyeing. More specifically, even in two or more individuals whose hair colors after dying are almost the same "somewhat reddish light brown" as determined by visual recognition, colors of compositions that should be used for exactly returning each individual's hair to the color observed immediately after dyeing once the hair color has faded are different for an individual who has, for example, dyed her original blond hair "somewhat reddish light brown" and an individual who has dyed her original somewhat dark reddish brown hair "somewhat reddish light brown." The reason for this is that colors in the oxidative hair dye compositions used for each dye process were different from each other.

In the same regard, even in individuals whose hair colors are different from one another as determined by visual recognition, colors of compositions to be used for exactly returning to the color of hair observed immediately after hair dyeing when the hair color is faded may be the same, as long as the colors used in the oxidative hair dye compositions used to dye the hair were the same.

The corresponding relationship according to the present invention is the following:

Oxidative dye compositions having colors of various kinds are known.

When these respective colors are plotted in a color coordinate space ($L^*a^*b^*$ color space), the points can be divided into groups having a certain range within the space.

The way to divide into groups is exactly conducted, wherein the color of one color-revitalizing composition to be used corresponds to one group. The color of the color-revitalizing composition can also be represented as a certain range within the color coordinate space.

A further description of the invention is provided by the following examples:

Oxidative hair dye compositions whose colors fall within a range that $L^*$ is 15 to 47, $a^*$ is −2 to 8, and $b^*$ is 9 to 35 can be regarded as one group. Examples of the oxidative hair dye compositions included in this group include those sold under the color names of "LIGHT BROWN/LOREAL PREFERENCE 6 ($L^*=42$, $a^*=3$, $b^*=10$)", "MEDIUM BROWN/LOREAL PREFERENCE 5 ($L^*=35$, $a^*=3$, $b^*=10$)", "MEDIUM GOLDEN BROWN/LOREAL PREFERENCE 5G ($L^*=34$, $a^*=7$, $b^*=10$)", "DARK BROWN/LOREAL PREFERENCE 4($L^*=31$, $a^*=2$, $b^*=10$)", etc. A color-revitalizing composition of a color tone belonging in a circular range with a radius r of 11, preferably a radius r of 4, centering around a point of $L^*=51$, $a^*=8$ and $b^*=19$ is used against hair dyed with an oxidative hair dye composition included in this group, whereby the hair color can be nearly revitalized to a color observed immediately after hair dyeing to bring back the color tone and the satisfaction generally felt right after hair dyeing.

Oxidative hair dye compositions whose colors fall within a range that $L^*$ is 47 to 90, $a^*$ is −2 to 8, and $b^*$ is 9 to 35 can be regarded as another group. Examples of the oxidative hair dye compositions included in this group include those sold under the color names of "LIGHTEST GOLDEN BLOND/LOREAL PREFERENCE 9G ($L^*=62$, $a^*=7$, $b^*=15$)", "GOLDEN BLOND/LOREAL PREFERENCE 8G ($L^*=63$, $a^*=5$, $b^*=14$)", etc. A color-revitalizing composition of a color tone belonging in a circular range with a radius r of 6, preferably a radius r of 4, centering around a point of $L^*=76$, $a^*=2$ and $b^*=21$ is used against hair dyed with an oxidative hair dye composition included in this group, whereby the hair color can be nearly revitalized to a color observed immediately after hair dyeing to bring back the color tone and the satisfaction generally felt right after hair dyeing.

Oxidative hair dye compositions whose colors fall within a range that $L^*$ is 15 to 43, $a^*$ is −2 to 8, and $b^*$ is 0 to 9 can be regarded as a further group. Examples of the oxidative hair dye compositions included in this group include those sold under the color names of "LIGHT ASH BROWN/LOREAL PREFERENCE 6A ($L^*=41$, $a^*=5$, $b^*=7$)", "MEDIUM ASH BROWN/LOREAL PREFERENCE 5A ($L^*=33$, $a^*=5$, $b^*=7$)", "DARK ASH BROWN/LOREAL PREFERENCE 4A ($L^*=28$, $a^*=4$, $b^*=5$)", etc. A color-revitalizing composition of a color tone belonging in a circular range with a radius r of 12, preferably a radius r of 4, centering around a point of $L^*=53$, $a^*=4$ and $b^*=18$ is used against hair dyed with an oxidative hair dye composition included in this group, whereby the hair color can be nearly revitalized to a color observed immediately after hair dyeing to bring back the color tone and a satisfaction generally felt right after hair dyeing.

Oxidative hair dye compositions whose colors fall within a range that $L^*$ is 43 to 52, $a^*$ is −2 to 8, and $b^*$ is 0 to 9 can be regarded as a still further group. Examples of the oxidative hair dye compositions included in this group include those sold under the color names of "DARK ASH BLOND/LOREAL PREFERENCE 7A ($L^*=44$, $a^*=5$, $b^*=7$)", etc. A color-revitalizing composition of a color tone belonging in a circular range with a radius r of 9, preferably a radius r of 4, centering around a point of $L^*=78$, $a^*=2$ and $b^*=0$ is used against hair dyed with an oxidative hair dye composition included in this group, whereby the hair color can be nearly revitalized to a color observed immediately after hair dyeing to bring back the color tone and a satisfaction generally felt right after hair dyeing.

Oxidative hair dye compositions whose colors fall within a range that $L^*$ is 52 to 90, $a^*$ is −2 to 8, and $b^*$ is 0 to 9 can be regarded as a yet still further group. Examples of the oxidative hair dye compositions included in this group include those sold under the color names of "EXTRA LIGHT ASH BLOND/LOREAL PREFERENCE LB01 ($L^*=83$, $a^*=0$, $b^*=4$)", "EXTRA LIGHT ASH BLOND/LOREAL PREFERENCE 9½A ($L^*=73$, $a^*=4$, $b^*=6$)", "EXTRA LIGHT NATURAL BLOND/LOREAL PREFERENCE LB02 ($L^*=82$, $a^*=1$, $b^*=6$)", "LIGHTEST ASH BLOND/LOREAL PREFERENCE 9A ($L^*=63$, $a^*=5$, $b^*=4$)", "LIGHTEST NATURAL BLOND/LOREAL PREFERENCE 9½NB ($L^*=87$, $a^*=-1$, $b^*=7$)", "ASH BLOND/LOREAL PREFERENCE 8A ($L^*=58$, $a^*=6$, $b^*=4$)", "NATURAL BLOND/LOREAL PREFERENCE 9 ($L^*=64$, $a^*=5$, $b^*=7$)", etc. A color-revitalizing composition of a color tone belonging in a circular range with a radius r of 5, preferably a radius r of 4, centering around a point of $L^*=82$, $a^*=0$ and $b^*=5$ is used against hair dyed with an oxidative hair dye composition included in this group, whereby the hair color can be nearly revitalized to a color observed immediately after hair dyeing to bring back the color tone and the satisfaction generally felt right after hair dyeing.

Oxidative hair dye compositions whose colors fall within a range that $L^*$ is 15 to 46, $a^*$ is 8 to 12, and $b^*$ is 0 to 35 can be regarded as a yet still further group. Examples of the oxidative hair dye compositions included in this group include those sold under the color names of "LIGHT AUBURN/LOREAL PREFERENCE 6R ($L^*=46$, $a^*=10$, $b^*=15$)", "DARK REDDISH BLOND/LOREAL PREFERENCE 7SF ($L^*=45$, $a^*=9$, $b^*=12$)", etc. A color-revitalizing composition of a color tone belonging in a circular range with a radius r of 4, preferably a radius r of 2, centering around a point of $L^*=55$, $a^*=25$ and $b^*=16$ is used against hair dyed with an oxidative hair dye composition included in this group, whereby the hair color can be nearly revitalized to a color observed immediately after hair dyeing to bring back the color tone and the satisfaction generally felt right after hair dyeing.

Oxidative hair dye compositions whose colors fall within a range that L* is 15 to 46, a* is 12 to 30, and b* is 0 to 35 can be regarded as a yet still further group. Examples of the oxidative hair dye compositions included in this group include those sold under the color names of "INTENSE DARK RED/LOREAL PREFERENCE RR04 (L*=28, a*=13, b*=6)", "INTENSE RED/LOREAL PREFERENCE RR06 (L*=33, a*=20, b*=8)", "INTENSE RED KAPPA/ LOREAL PREFERENCE RR07 (L*=43, a*=22, b*=20)", etc. A color-revitalizing composition of a color tone belonging in a circular range with a radius r of 8, preferably a radius r of 4, centering around a point of L*=50, a*=32 and b*=10 is used against hair dyed with an oxidative hair dye composition included in this group, whereby the hair color can be nearly revitalized to a color observed immediately after hair dyeing to bring back the color tone and the satisfaction generally felt right after the hair dyeing.

Oxidative hair dye compositions whose colors fall within a range that L* is 46 to 90, a* is 8 to 30, and b* is 0 to 35 can be regarded as a yet still further group. Examples of the oxidative hair dye compositions included in this group include those sold under the color names of "LIGHTEST AUBURN/LOREAL PREFERENCE 7LA (L*=54, a*=9, b*=14)", "REDDISH BLOND/LOREAL PREFERENCE 8BA (L*=55, a*=11, b*=18)", "LIGHT GOLDEN REDDISH BLOND/LOREAL PREFERENCE 9GR (L*=61, a*=10, b*=15)", etc. A color-revitalizing composition of a color tone belonging in a circular range with a radius r of 8, preferably a radius r of 4, centering around a point of L*=55, a*=17 and b*=23 is used against hair dyed with an oxidative hair dye composition included in this group, whereby the hair color can be nearly revitalized to a color observed immediately after hair dyeing to bring back the color tone and the satisfaction generally felt right after hair dyeing.

In such a manner, the system and method according to the present invention can cope with the colors of the various oxidative hair dye compositions.

The number of colors of the oxidative hair dye compositions and the number of colors of color-revitalizing compositions can be made the relation of many to one, and so color matching can be simplified, and color selection can be conducted with ease and accuracy.

The word "color" as used herein is defined as a value in the color coordinate space (L*a*b* color space) in the following manner.

11 g of an oxidative hair dye composition or color-revitalizing composition is evenly applied to a bundle of white goat hair, weighing 1 g (obtained by washing hair of a white goat aged 2 years or older inhabited in a Tibet autonomous district of China, evenly cut into lengths of 10 cm and bundled gram by gram; having a color within a range that L* is 84 to 87, a* is −3 to 0, and b* is 9 to 12), the bundle is left at rest for 20 minutes in a thermostatic chamber controlled at 30° C., is rinsed out with hot water at 40° C., is shampooed, rinse-treated and dried. The color of the goat hair thus treated is measured in terms of L*a*b* values by a chroma meter (CR-200, MINOLTA CO., LTD.).

Examples of the color-revitalizing composition in the color-revitalizing system and method according to an embodiment of the present invention include compositions comprising an acid direct dye and an organic solvent and having an acidic pH.

Examples of the acid direct dye include Yellow No. 203 (D & C Yellow No. 10 Color Index (CI) given as (CI 47005)), Orange No. 205 (D & C Orange No 4 (CI 15510)), Red No. 227 (D & C Red No. 33 (CI (Color index) 17200)), Violet No. 401 (Ext. D & C Violet No. 2 (CI 607301)) and Black No. 401 (CI 20470). Examples of the organic solvent include benzyl alcohol, 2-benzyloxyethanol, propylene carbonate gamma-butyrolactone and N-methylpyrrolidone. Ethanol, propylene glycol or the like is preferably used as a solubilizing agent for the organic solvent in water. The compositions are preferably kept at pH 2 to 6, particularly pH 2 to 5, and more particularly pH 2 to 4. The adjustment of the pH may be conducted in accordance with any known method. A thickener may be added to prevent running and the like, thus facilitating its application to hair.

When a composition comprising an acid direct dye and/or an organic solvent and having an acidic pH is used as the color-revitalizing composition, the dullness of hair is improved, and a feeling of transparency, luster, shine, structure, body, deep shade and manageability is imparted to the hair.

Color-revitalizing compositions according to another embodiment of the invention include compositions comprising a basic direct dye and having a weakly acidic to a basic pH. Examples of the basic direct dye include basic dyes included in "International Cosmetic Ingredient Dictionary and Handbook", 8th Ed. and sold under the trade name of Alianol and dyes described in European Patent No. 970685, the entire contents of which is incorporated herein by reference. The compositions are preferably kept at a pH of 6 to 12, and more particularly at a pH of 8 to 11. The adjustment of the pH may be conducted in accordance with any known method. A thickener may be added to prevent running and the like, thus facilitating its application to hair.

In the color-revitalizing compositions used in the present invention, cosmetic ingredients commonly used in cosmetic compositions may be incorporated, as needed. In addition, it is preferred that propylene carbonate is included. Propylene carbonate aids in the penetration of the dye into hair and improves the texture and quality of hair.

The color-revitalizing compositions used in the present invention may be prepared in the form of a gel, a cream, a liquid, a foam or the like and may also be provided in the form of an aerosol.

Methods for applying the color-revitalizing composition used in the present invention to hair include a method in which dry hair or wetted hair in such a degree that wet hair is wiped with a towel is coated with a proper amount of the composition to evenly spread the composition throughout the hair, left to stand for 3 to 45 minutes, rinsed out with warm water, optionally shampooed and rinsed, and then dried, and a method in which hair that has been shampooed and wiped with a towel is coated with a proper amount of the composition to evenly spread the composition throughout the hair, left to stand for 3 to 45 minutes, rinsed out with warm water, optionally shampooed and rinsed, and then dried.

The system and method of the invention is simple and does not require large amounts of time to carry out. An example of a protocol for applying the color revitalizing composition of the invention includes:

Using gloves, uniformly apply to damp hair; leave in for 10 minutes; shampoo out; and proceed with normal hair care routine. Use weekly, or as necessary to maintain beautiful hair color.

If desired, one can preview the results prior to use by doing a simple strand test as follows:

1) Dampen an underneath section of hair (½ to 1 inch);
2) Apply the color revitalization composition (about a dime size) and massage in thoroughly;

3) After 10 minutes, shampoo and rinse;

4) Dry and inspect hair to confirm the color restoration.

Another example of a protocol for applying the color revitalizing composition of the invention includes:

Dampen hair (not soaking wet) at sink or in shower.

Put on gloves and squeeze about a half-dollar sized amount into palm of hand (about 2 tablespoons). Adjust the amount used as necessary for length of type of hair.

Massage into hair.

Rub in until all hair is uniformly covered.

Leave in hair for 10 minutes.

Shampoo the color-revitalizing composition out of hair using shampoo, and rinse until water is free from coloration.

Proceed with normal hair care and styling routine.

Use about once a week to maintain a beautiful, shiny, fresh-colored look. More frequent use will increase the coloring effect, if desired.

EXAMPLES

According to the color-revitalizing system and method of the present invention, the faded color tone of hair dyed with an oxidative hair dye composition can be revitalized to a color tone observed immediately after hair dyeing with ease without damaging the hair.

Colors of oxidative hair dye compositions can be divided into 5 to 12 groups, preferably 6 to 10 groups, and a color-revitalizing composition corresponding to each group is determined, thus permitting selection of color selection with ease and accuracy.

Examples 1 to 8

Compositions 1–8 shown in Table 1 (below) were prepared as color-revitalizing compositions. Except for the L* a* b* values, all amounts are % by weight unless otherwise specified.

dyed with a "DARK BROWN/LOREAL PREFERENCE 4", all coming to feel their hair colors dissatisfactory, used the color-revitalizing composition of the invention (composition according to Example 1 in Table 1). All of the individuals had a feeling of satisfaction (color, feel, etc.) after use.

Example 10

Four individuals who entered upon the ninth day after having their hair dyed with a "LIGHT GOLDEN BLOND/ LOREAL PREFERENCE 9G", and four individuals who entered upon the ninth day after having their hair dyed with a "GOLDEN BLOND/LOREAL PREFERENCE 8G", all coming to feel their hair colors dissatisfactory, used the color-revitalizing composition (composition according to Example 2 in Table 1). All of the individuals had a feeling of satisfaction (color, feel, etc.) after use.

Example 11

Three individuals who entered upon the fourteenth day after having their hair dyed with a "LIGHT ASH BROWN/ LOREAL PREFERENCE 6A", three individuals who entered upon the fourteenth day after having their hair dyed with a "MEDIUM ASH BROWN/LOREAL PREFERENCE 5A", and three individuals who entered upon the fourteenth day after having their hair dyed with a "DARK ASH BROWN/LOREAL PREFERENCE 4A", all coming to feel their hair colors dissatisfactory, used the color-revitalizing composition (composition according to Example 3 in Table 1). All of the individuals had a feeling of satisfaction (color, feel, etc.) after use.

Example 12

Seven individuals who entered upon the tenth day after having their hair dyed with a "DARK ASH BLOND/ LOREAL PREFERENCE 7A" and came to feel their hair colors dissatisfactory used the color-revitalizing composition (composition according to Example 4 in Table 1). All of the individuals had a feeling of satisfaction (color, feel, etc.) after use.

TABLE 1

| Example | 1 | 2 | 3 | 4 | 5 | 6 | 7 | 8 |
|---|---|---|---|---|---|---|---|---|
| Propylene carbonate | 25 | 25 | 25 | 25 | 25 | 25 | 25 | 25 |
| 95° ethanol | 5 | 5 | 5 | 5 | 5 | 5 | 5 | 5 |
| Xanthan gum | 1.5 | 1.5 | 1.5 | 1.5 | 1.5 | 1.5 | 1.5 | 1.5 |
| Polyether-modified silicone (Dimethicone Copolymer) | 1.5 | 1.5 | 1.5 | 1.5 | 1.5 | 1.5 | 1.5 | 1.5 |
| Lactic acid (90 wt. %) | 5 | 5 | 5 | 5 | 5 | 5 | 5 | 5 |
| Aqueous sodium hydroxide (48 wt. %) | Amount to pH 3 | Amount to pH 3 | Amount to pH 3 | Amount to pH 3 | Amount to pH 3 | Amount to pH 3 | Amount to pH 3 | Amount to pH 3 |
| Perfume base | q.s. | q.s. | q.s. | q.s. | q.s. | q.s. | q.s. | q.s. |
| Orange No. 205 | 0.072 | 0.0076 | 0.044 | 0 | 0 | 0.066 | 0.066 | 0.07 |
| Violet No. 401 | 0.089 | 0.0075 | 0.095 | 0.01 | 0.005 | 0.019 | 0.019 | 0.31 |
| Yellow No. 203 | 0.061 | 0.0086 | 0.083 | 0 | 0 | 0 | 0 | 0.21 |
| Red No. 227 | 0 | 0 | 0 | 0 | 0 | 0.018 | 0.045 | 0.008 |
| Water | Balance | Balance | Balance | Balance | Balance | Balance | Balance | Balance |
| L* | 51 | 76 | 53 | 78 | 82 | 55 | 50 | 55 |
| a* | 8 | 2 | 4 | 2 | 0 | 25 | 32 | 17 |
| b* | 19 | 21 | 18 | 0 | 5 | 16 | 10 | 23 |

Example 9

Two individuals who entered upon the seventh day after having their hair dyed with a "LIGHT BROWN/LOREAL PREFERENCE 6", two individuals who entered upon the seventh day after having their hair dyed with a "MEDIUM BROWN/LOREAL PREFERENCE 5G", and two individuals who entered upon the seventh day after having their hair Example 13

One individual who entered upon the eighth day after having his/her hair dyed with an "EXTRA LIGHT ASH BLOND/LOREAL PREFERENCE LB01", one individual who entered upon the eighth day after having his/her hair dyed with an "EXTRA LIGHT ASH BLOND/LOREAL PREFERENCE 9½A", one individual who entered upon the eighth day after having his/her hair dyed with an "EXTRA LIGHT NATURAL BLOND/LOREAL PREFERENCE LB02", one individual who entered upon the eighth day after having his/her hair dyed with a "LIGHTEST ASH BLOND/LOREAL PREFERENCE 9A", one individual who entered upon the eighth day after having his/her hair dyed with a "LIGHTEST NATURAL BLOND/LOREAL PREFERENCE 9½NB", one individual who entered upon the eighth day after having his/her hair dyed with an "ASH BLOND/LOREAL PREFERENCE 8A", and one individual who entered upon the eighth day after having his/her hair dyed with a "NATURAL BLOND/LOREAL PREFERENCE 9", all coming to feel their hair colors dissatisfactory, used the color-revitalizing composition (composition according to Example 5 in Table 1). All of the individuals had a feeling of satisfaction (color, feel, etc.) after use.

Example 14

Four individuals who entered upon the ninth day after having their hair dyed with a "LIGHT AUBURN/LOREAL PREFERENCE 6R", and four individuals who entered upon the ninth day after having their hair dyed with a "DARK REDDISH BLOND/LOREAL PREFERENCE 7SF", all coming to feel their hair colors dissatisfactory, used the color-revitalizing composition (composition according to Example 6 in Table 1). All of the individuals had a feeling of satisfaction (color, feel, etc.) after use.

Example 15

Three individuals who entered upon the seventh day after having their hair dyed with an "INTENSE DARK RED/LOREAL PREFERENCE RR04", three individuals who entered upon the seventh day after having their hair dyed with an "INTENSE RED/LOREAL PREFERENCE RR06", and three individuals who entered upon the seventh day after having their hair dyed with an "INTENSE RED KAPPA/LOREAL PREFERENCE RR07", all coming to feel their hair colors dissatisfactory, used the color-revitalizing composition (composition according to Example 7 in Table 1). All of the individuals had a feeling of satisfaction (color, feel, etc.) after use.

Example 16

Three individuals who entered upon the twelfth day after having their hair dyed with a "LIGHTEST AUBURN/LOREAL PREFERENCE 7LA", three individuals who entered upon the twelfth day after having their hair dyed with a "REDDISH BLOND/LOREAL PREFERENCE 8BA", and three individuals who entered upon the twelfth day after having their hair dyed with a "LIGHT GOLDEN REDDISH BLOND/LOREAL PREFERENCE 9GR", all coming to feel their hair colors dissatisfactory, used the color-revitalizing composition (composition according to Example 8 in Table 1). All of the individuals had a feeling of satisfaction (color, feel, etc.) after use.

Although the present invention has been fully described by way of examples, it is to be noted that various changes and modifications will be apparent to those skilled in the art. It is therefore intended that the foregoing detailed description be understood from the following claims, including all equivalents, which are intended to define the scope of the invention. Therefore, unless such changes and modifications depart from the scope of the invention, they should be construed as being included therein.

What is claimed is:

1. A method for color-revitalizing color tone of hair, comprising:

applying a color-revitalizing composition to hair that has previously been dyed with an oxidative hair dye composition, said color-revitalizing composition (a) having a color determined by a color of said oxidative hair dye composition and (b) containing at least one direct dye;

thereby revitalizing the color tone obtained by the hair after being dyed with said oxidative hair dye composition; and wherein a color-revitalizing composition of a color tone belonging in a circular range with a radius r of 11 centering around a point of $L^*=51$, $a^*=8$ and $b^*=19$ in a color coordinate space ($L^*$ $a^*$ $b^*$ color space) is used when the color of said oxidative hair dye composition falls within a range of $L^*$ is 15 to 47, $a^*$ is −2 to 8, and $b^*$ is 9 to 30 in the color coordinate space, and wherein colors of the respective compositions are determined by colors obtained when white goat hair is dyed with such compositions.

2. A method for color-revitalizing a color tone of hair, comprising:

applying a color-revitalizing composition to hair that has previously been dyed with an oxidative hair dye composition, said color-revitalizing composition (a) having a color determined by a color of said oxidative hair dye composition and (b) containing at least one direct dye;

thereby revitalizing the color tone obtained by the hair after being dyed with said oxidative hair dye composition; and wherein a color-revitalizing composition of a color tone belonging in a circular range with a radius r of 6 centering around a point of $L^*$ 76, $a^*=2$ and $b^*=21$ in a color coordinate space ($L^*a^*b^*$ color space) is used when the color of said oxidative hair dye composition falls within a range that $L^*$ is 47 to 90, $a^*$ is −2 to 8, and $b^*$ is 9 to 35 in the color coordinate space, and wherein colors of the respective compositions are determined by colors obtained when white goat hair is dyed with such compositions.

3. A method for color-revitalizing a color tone of hair, comprising:

applying a color-revitalizing composition to hair that has previously been dyed with an oxidative hair dye composition, said color-revitalizing composition (a) having a color determined by a color of said oxidative hair dye composition and (b) containing at least one direct dye;

thereby revitalizing the color tone obtained by the hair after being dyed with said oxidative hair dye composition; and wherein a color-revitalizing composition of a color tone belonging in a circular range with a radius r of 12 centering around a point of $L^*$ 53, $a^*$ 4 and $b^*=18$ in a color coordinate space ($L^*$ a $b^*$ color space) is used when the color of said oxidative hair dye composition falls within a range that $L^*$ is 15 to 43, $a^*$ is −2 to 8, and $b^*$ is 0 to 9 in the color coordinate space, and wherein colors of the respective compositions are determined by colors obtained when white goat hair is dyed with such compositions.

4. A method for color-revitalizing a color tone of hair, comprising:
applying a color-revitalizing composition to hair that has previously been dyed with an oxidative hair dye composition, said color-revitalizing composition (a) having a color determined by a color of said oxidative hair dye composition and (b) containing at least one direct dye;
thereby revitalizing the color tone obtained by the hair after being dyed with said oxidative hair dye composition; and
wherein a color-revitalizing composition of a color tone belonging in a circular range with a radius r of 9 centering around a point of $L^*=78$, $a^*=2$ and $b^*$ 0 in a color coordinate space ($L^*$ $a^*$ $b^*$ color space) is used when the color of said oxidative hair dye composition falls within a range that $L^*$ is 43 to 52, $a^*$ is −2 to 8, and $b^*$ is 0 to 9 in the color coordinate space, and wherein colors of the respective compositions are determined by colors obtained when white goat hair is dyed with such compositions.

5. A method for color-revitalizing a color tone of hair, comprising:
applying a color-revitalizing composition to hair that has previously been dyed with an oxidative hair dye composition, said color-revitalizing composition (a) having a color determined by a color of said oxidative hair dye composition and (b) containing at least one direct dye;
thereby revitalizing the color tone obtained by the hair after being dyed with said oxidative hair dye composition; and
wherein a color-revitalizing composition of a color tone belonging in a circular range with a radius r of 5 centering around a point of $L^*=82$, $a^*=0$ and $b^*=5$ in a color coordinate space ($L^*$ $a^*$ $b^*$ color space) is used when the color of said oxidative hair dye composition falls within the range of $L^*$ is 52 to 90, $a^*$ is −2 to 8, and $b^*$ is 0 to 9 in the color coordinate space, and wherein colors of the respective compositions are determined by colors obtained when white goat hair is dyed with such compositions.

6. A method for color-revitalizing a color tone of hair, comprising:
applying a color-revitalizing composition to hair that has previously been dyed with an oxidative hair dye composition, said color-revitalizing composition (a) having a color determined by a color of said oxidative hair dye composition and (b) containing at least one direct dye;
thereby revitalizing the color tone obtained by the hair after being dyed with said oxidative hair dye composition; and
wherein a color-revitalizing composition of a color tone belonging in a circular range with a radius r of 4 centering around a point of $L^*=55$, $a^*=25$ and $b^*=16$ in a color coordinate space ($L^*$ $a^*$ $b^*$ color space) is used when the color of said oxidative hair dye composition falls within a range that $L^*$ is 15 to 50, $a^*$ is 8 to 12, and $b^*$ is 0 to 35 in the color coordinate space, and wherein colors of the respective compositions are determined by colors obtained when white goat hair is dyed with such compositions.

7. A method for color-revitalizing a color tone of hair, comprising:
applying a color-revitalizing composition to hair that has previously been dyed with an oxidative hair dye composition, said color-revitalizing composition (a) having a color determined by a color of said oxidative hair dye composition and (b) containing at least one direct dye;
thereby revitalizing the color tone obtained by the hair after being dyed with said oxidative hair dye composition; and
wherein a color-revitalizing composition of a color tone belonging in a circular range with a radius r of 8 centering around a point of $L^*=50$, $a^*=32$ and $b^*=10$ in a color coordinate space ($L^*$ $a^*$ $b^*$ color space) is used when the color of said oxidative hair dye composition falls within a range that $L^*$ is 15 to 46, $a^*$ is 12 to 30, and $b^*$ is 0 to 35 in the color coordinate space, and wherein colors of the respective compositions are determined by colors obtained when white goat hair is dyed with such compositions.

8. A method for color-revitalizing a color tone of hair, comprising:
applying a color-revitalizing composition to hair that has previously been dyed with an oxidative hair dye composition, said color-revitalizing composition (a) having a color determined by a color of said oxidative hair dye composition and (b) containing at least one direct dye;
thereby revitalizing the color tone obtained by the hair after being dyed with said oxidative hair dye composition; and
wherein a color-revitalizing composition of a color tone belonging in a circular range with a radius r of 8 centering around a point of $L^*=55$, $a^*=17$ and $b^*=23$ in a color coordinate ($L^*$ $a^*$ $b^*$ color space) is used when the color of said oxidative hair dye composition falls within a range that $L^*$ is 46 to 90, $a^*$ is 8 to 30, and $b^*$ is 0 to 35 in the color coordinate space, and wherein colors of the respective compositions are determined by colors obtained when white goat hair is dyed with such compositions.

9. The method of claim 1 wherein said direct dye is an acid direct dye and said color revitalizing composition comprises an organic solvent, wherein said color revitalizing composition has a pH of 2–6.

10. The method of claim 2 wherein said direct dye is an acid direct dye and said color revitalizing composition comprises an organic solvent, wherein said color revitalizing composition has a pH of 2–6.

11. The method of claim 3 wherein said direct dye is an acid direct dye and said color revitalizing composition comprises an organic solvent, wherein said color revitalizing composition has a pH of 2–6.

12. The method of claim 4 wherein said direct dye is an acid direct dye and said color revitalizing composition comprises an organic solvent, wherein said color revitalizing composition has a pH of 2–6.

13. The method of claim 5 wherein said direct dye is an acid direct dye and said color revitalizing composition comprises an organic solvent, wherein said color revitalizing composition has a pH of 2–6.

14. The method of claim 6 wherein said direct dye is an acid direct dye and said color revitalizing composition comprises an organic solvent, wherein said color revitalizing composition has a pH of 2–6.

15. The method of claim 7 wherein said direct dye is an acid direct dye and said color revitalizing composition comprises an organic solvent, wherein said color revitalizing composition has a pH of 2–6.

16. The method of claim 8 wherein said direct dye is an acid direct dye and said color revitalizing composition comprises an organic solvent, wherein said color revitalizing composition has a pH of 2–6.

17. The method of claim 1 wherein said direct dye is a basic direct dye and said color revitalizing composition comprises an organic solvent, and wherein said color revitalizing composition has a pH of 6–12.

18. The method of claim 2 wherein said direct dye is a basic direct dye and said color revitalizing composition comprises an organic solvent, and wherein said color revitalizing composition has a pH of 6–12.

19. The method of claim 3 wherein said direct dye is a basic direct dye and said color revitalizing composition comprises an organic solvent, and wherein said color revitalizing composition has a pH of 6–12.

20. The method of claim 4 wherein said direct dye is a basic direct dye and said color revitalizing composition comprises an organic solvent, and wherein said color revitalizing composition has a pH of 6–12.

21. The method of claim 5 wherein said direct dye is a basic direct dye and said color revitalizing composition comprises an organic solvent, and wherein said color revitalizing composition has a pH of 6–12.

22. The method of claim 6 wherein said direct dye is a basic direct dye and said color revitalizing composition comprises an organic solvent, and wherein said color revitalizing composition has a pH of 6–12.

23. The method of claim 7 wherein said direct dye is a basic direct dye and said color revitalizing composition comprises an organic solvent, and wherein said color revitalizing composition has a pH of 6–12.

24. The method of claim 8 wherein said direct dye is a basic direct dye and said color revitalizing composition comprises an organic solvent, and wherein said color revitalizing composition has a pH of 6–12.

* * * * *

UNITED STATES PATENT AND TRADEMARK OFFICE
CERTIFICATE OF CORRECTION

PATENT NO. : 6,908,491 B2
DATED : June 21, 2005
INVENTOR(S) : Fischer et al.

It is certified that error appears in the above-identified patent and that said Letters Patent is hereby corrected as shown below:

Column 12,
Line 38, "L* 76, a*= 2 and b*= 21" should read -- L*=76, a*=2 and b*= 21" --.
Line 60, "L* 53, a*4" should read -- L*=53, a*=4" --.

Signed and Sealed this

Sixth Day of September, 2005

JON W. DUDAS
*Director of the United States Patent and Trademark Office*

UNITED STATES PATENT AND TRADEMARK OFFICE
CERTIFICATE OF CORRECTION

PATENT NO.       : 6,908,491 B2                                Page 1 of 1
APPLICATION NO.  : 09/983070
DATED            : June 21, 2005
INVENTOR(S)      : Vince Fischer et al.

It is certified that error appears in the above-identified patent and that said Letters Patent is hereby corrected as shown below:

On the Title Page, the Assignee information should read:

(73) Assignee: KAO Corporation
     Tokyo, 103-8210 JAPAN and

The Andrew Jergens Company
     Cincinatti, OH (US)

Signed and Sealed this

Twenty-second Day of May, 2007

JON W. DUDAS
*Director of the United States Patent and Trademark Office*

UNITED STATES PATENT AND TRADEMARK OFFICE
CERTIFICATE OF CORRECTION

PATENT NO.        : 6,908,491 B2                                              Page 1 of 1
APPLICATION NO.   : 09/983070
DATED             : June 21, 2005
INVENTOR(S)       : Vince Fischer et al.

It is certified that error appears in the above-identified patent and that said Letters Patent is hereby corrected as shown below:

On the Title Page, the Assignee information should read:

(73) Assignee: KAO Corporation
               Tokyo, 103-8210 JAPAN and

The Andrew Jergens Company
               Cincinatti, OH (US)

Signed and Sealed this

Twelfth Day of June, 2007

JON W. DUDAS
*Director of the United States Patent and Trademark Office*